United States Patent
Spijkerman et al.

(10) Patent No.: US 11,220,608 B2
(45) Date of Patent: Jan. 11, 2022

(54) POWDER MIXTURE COMPRISING ORGANIC PEROXIDE

(71) Applicant: NOURYON CHEMICALS INTERNATIONAL B.V., Arnhem (NL)

(72) Inventors: Geesje Klasina Spijkerman, Deventer (NL); Martin Hermanus Maria Jansen, Wijhe (NL); Auke Gerardus Talma, Bathmen (NL); Antonie Den Braber, Arnhem (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/753,581

(22) PCT Filed: Oct. 2, 2018

(86) PCT No.: PCT/EP2018/076736
§ 371 (c)(1),
(2) Date: Apr. 3, 2020

(87) PCT Pub. No.: WO2019/068683
PCT Pub. Date: Apr. 11, 2019

(65) Prior Publication Data
US 2020/0299522 A1    Sep. 24, 2020

(51) Int. Cl.
| | |
|---|---|
| C09D 5/18 | (2006.01) |
| C09D 7/63 | (2018.01) |
| C07C 407/00 | (2006.01) |
| C07C 409/34 | (2006.01) |
| C08K 5/14 | (2006.01) |
| C08K 13/02 | (2006.01) |
| C08K 3/22 | (2006.01) |

(52) U.S. Cl.
CPC ............ *C09D 5/18* (2013.01); *C07C 407/006* (2013.01); *C07C 409/34* (2013.01); *C09D 7/63* (2018.01); *C08K 5/14* (2013.01); *C08K 13/02* (2013.01); *C08K 2003/2224* (2013.01); *C08K 2003/2227* (2013.01)

(58) Field of Classification Search
CPC ... C07C 409/00; C07C 409/32; C07C 409/34; C07C 407/00; C07C 407/003; C07C 407/006; C08F 4/32; C08F 4/34; C08F 4/36; C08F 4/38; C08K 5/14; C08K 3/22; C08K 2003/2224; C08K 2003/2227; C08K 9/08
USPC ................ 252/186.26, 186.42; 568/559, 566
See application file for complete search history.

(56) References Cited

U.S. PATENT DOCUMENTS

| | | | | |
|---|---|---|---|---|
| 2,207,737 | A * | 7/1940 | Hooft | C01F 11/46 252/186.42 |
| 2,272,577 | A * | 2/1942 | Penn | A21D 2/20 426/258 |
| 2,453,071 | A * | 11/1948 | Hyatt | C07C 409/34 427/212 |
| 3,462,370 | A * | 8/1969 | Brossmann | C07C 409/34 502/2 |
| 3,731,791 | A * | 5/1973 | Fourcade | C04B 40/0666 206/219 |
| 4,977,240 | A * | 12/1990 | Ishiwatari | C08F 299/045 523/500 |
| 5,168,280 | A * | 12/1992 | Blaese | H01Q 1/1285 343/715 |
| 5,258,071 | A * | 11/1993 | LaRoche | C08F 2/44 106/441 |
| 5,370,818 | A * | 12/1994 | Schleifstein | C08K 7/16 252/186.25 |
| 6,280,839 | B1 * | 8/2001 | Brown | B32B 5/28 106/18.12 |
| 10,287,405 | B2 * | 5/2019 | Nishiguchi | B29B 7/005 |
| 10,626,263 | B2 * | 4/2020 | Beek | C08F 210/16 |
| 2001/0044497 | A1 | 11/2001 | Myers | |
| 2010/0209705 | A1* | 8/2010 | Lin | C08L 51/06 428/391 |
| 2019/0248983 | A1 | 8/2019 | Nagl et al. | |
| 2020/0369856 | A1* | 11/2020 | Beek | C08K 5/18 |

FOREIGN PATENT DOCUMENTS

| | | | | |
|---|---|---|---|---|
| CN | 110615919 A | * | 12/2019 | |
| DE | 102015223051 A1 | | 5/2017 | |
| EP | 1233014 A1 | * | 8/2002 | ............... C08K 5/14 |
| JP | 2017066191 A | * | 4/2017 | |
| WO | 2016096779 A1 | | 6/2016 | |
| WO | WO-2016096779 A1 | * | 6/2016 | ............... C08F 2/44 |

OTHER PUBLICATIONS

Machine translated English language equivalent of JP 2017066191 (2017, pages).*
Machine translated English language equivalent of CN 110615919 (2019, pages).*

* cited by examiner

*Primary Examiner* — Brieann R Johnston
(74) *Attorney, Agent, or Firm* — Lorenz & Kopf, LLP

(57) ABSTRACT

Powder mixture comprising 20-80 wt % of one or more powdered organic peroxides selected from the group consisting of dibenzoyl peroxide and substituted dibenzoyl peroxides, 20-80 wt % of a powdered filler material, at least 60 wt %, thereof consisting of a solid inorganic flame retardant, and 0-20 wt % water.

16 Claims, No Drawings

POWDER MIXTURE COMPRISING ORGANIC PEROXIDE

CROSS-REFERENCE TO RELATED APPLICATION

This application is a U.S. National-Stage entry under 35 U.S.C. § 371 based on International Application No. PCT/EP2018/076736, filed Oct. 2, 2018, which was published under PCT Article 21(2) and which claims priority to European Application No. 17194732.8, filed Oct. 4, 2017, which are all hereby incorporated in their entirety by reference.

TECHNICAL FIELD

The present invention relates to a powder mixture comprising an organic peroxide. The invention also relates to a process for the preparation of such a mixture and its use in various applications, including coating compositions.

BACKGROUND

Organic peroxides are widely used in various applications, such as the initiation of polymerization reactions (for instance polymerization of (meth)acrylates, styrene, and vinyl chloride), the crosslinking of rubbers and elastomers, and the curing of (meth)acrylic resins, unsaturated polyester resins, and vinyl ester resins.

Organic peroxides are rather unstable compounds in the sense that they are prone to decomposition. It is this instability that makes them suitable for the initiation of radical polymerization and curing reactions. But this instability can also lead to safety hazards. Many organic peroxides need to be diluted in order to be allowed to be stored and transported in a safe manner.

This dilution, also called phlegmatization, can be done with a liquid phlegmatizer—resulting in a solution, paste, emulsion, or suspension of the peroxide in said phlegmatizer—or with a solid phlegmatizer. If the organic peroxide itself is in solid form, dilution with a solid phlegmatizer will give a physical blend of organic peroxide and solid phlegmatizer.

It is of course important that the phlegmatized organic peroxide is stable for a sufficiently long period, meaning that both components remain homogeneously mixed and do not segregate to form separate phases.

Dibenzoyl peroxide (BPO) is often phlegmatized with about 25 wt % water. The resulting water-containing BPO has the form of a powder. For various polymerization processes, such as, for instance, the curing or hardening of unsaturated polyester resin masses, the presence of such large amounts of water is unacceptable so that the water containing products are simply unsuitable for these purposes. For instance, the presence of moisture may form a haze or result in blistering of a coating.

A known solid phlegmatizer for solid organic peroxides is calcium carbonate. An advantage of calcium carbonate is that it is relatively cheap and easy to handle; disadvantages are its hygroscopy and acid sensitivity.

Its hygroscopic properties make this material less suitable as a phlegmatizer for (substituted) dibenzoyl peroxides, as it may lead to (severe) caking of the formulation. In addition, when used in coating compositions, the coating compositions become sensitive to water, humid environment, and stains. This problem also exists with other hygroscopic materials, such as magnesium sulphate.

Its acid sensitivity makes $CaCO_3$ also less suitable in coating applications, more in particular for coatings that may come into contact with acids or that contain acidic ingredients. For instance, contact between $CaCO_3$-containing coatings and acid leads to a reaction that will deteriorate the coating and lead to the evolution of $CO_2$ from the coating. This is evidently undesired and makes $CaCO_3$-containing peroxide compositions unsuitable for use in coatings that may come into contact with acids. It also limits the choice of the other ingredients of the coating composition: they should be non-acidic.

The same problems will also be encountered with peroxide formulations containing other carbonate salts, such as magnesium carbonate or barium carbonate.

As a solution to this problem, WO 2016/096779 proposes phlegmatization of (substituted) dibenzoyl peroxides with barium sulphate. $BaSO_4$ is neither hygroscopic, nor acid sensitive, and the small primary particles of this material are transparent and therefore ideal for application in coating compositions and transparent composite systems.

However, it has now been found that such $BaSO_4$-based compositions still bear significant safety risks, especially when its water content is below 10 wt %. Even when a $BaSO_4$-containing powder mixture contains sufficient water upon preparation, it will dry out during storage, meaning that the safety risks will increase with storage time.

It is therefore an object of the present invention to provide a powdery (substituted) dibenzoyl peroxide formulation that is safer than the above $BaSO_4$-based compositions at low water content. In other words: the object is to provide a powdery (substituted) dibenzoyl peroxide formulation that is safer upon storage.

SUMMARY

This object has been achieved by using a solid inorganic flame retardant as the phlegmatizer.

The present invention therefore relates to a powder mixture comprising:
  20-80 wt % of one or more powdered organic peroxides selected from the group consisting of dibenzoyl peroxide and substituted dibenzoyl peroxides,
  20-80 wt % of a powdered filler material, at least 60 wt % thereof consisting of a solid inorganic flame retardant, and
  0-20 wt % water.

A process for preparing the powder mixture comprises the step of homogenizing 20-80 wt % of the one or more powdered organic peroxides and 20-80 wt % of the powdered filler material. In various embodiments the process comprises milling the organic peroxide in aqueous slurry to de-agglomerate the organic peroxide, removing water from the resulting de-agglomerated organic peroxide, and homogenizing the de-agglomerated organic peroxide and the powdered filler material.

In various embodiments, the powder mixture containing the peroxide is used as an initiator in a radical polymerization process, such as the curing of a coating composition.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

This powder mixture has the form of a powder; in other words: it is not a paste or suspension.

The powder mixture comprises at least 20 wt %, more preferably at least 30 wt %, even more preferably at least 40 wt %, and most preferably at least 50 wt % of the powdered filler material. The powder mixture comprises at most 80 wt %, and most preferably at most 70 wt % of the powdered filler material.

At least 60 wt %, more preferably at least 70 wt %, even more preferably at least 80 wt %, even more preferably at least 90 wt %, and most preferably 100 wt % of the powdered filler material consists of a solid inorganic flame retardant.

Examples of suitable solid inorganic flame retardants are aluminium trihydroxide (ATH), magnesium dihydroxide (MDH), hydrotalcite, organically modified hydrotalcite, and combinations thereof; including their hydrated forms. Hydrated forms include forms containing crystal water and/or adhering water.

The above materials act as flame retardants because of their endothermic decomposition at high temperatures, thereby liberating water. The heat absorbed by this decomposition retards the fire by delaying ignition of the associated substance. The water released dilutes combustible gases.

Preferred solid inorganic flame retardants are aluminium trihydroxide, magnesium dihydroxide, and combinations thereof; including their hydrated forms. Most preferred is aluminium trihydroxide. The latter compound is also referred to as aluminium trihydrate (ATH; Al(OH)$_3$).

ATH is found in nature as the mineral gibbsite (also known as hydrargillite), bayerite, doyleite and nordstrandite.

Suitable filler materials other than solid inorganic flame retardants are carbonates such as calcium carbonate, magnesium carbonate, and barium carbonate, silica, kaolinite, and calcium phosphate, with the remark that the carbonates are only suitable in acid-free environments.

The organic peroxide is selected from the group consisting of dibenzoyl peroxide and substituted dibenzoyl peroxides. Substituted dibenzoyl peroxides have the formula:

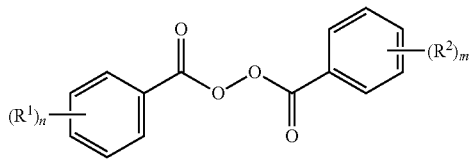

wherein each $R^1$ is individually selected from halogen (Cl, Br) atoms and linear or branched alkyl, aryl, or aralkyl groups with 1-10 carbon atoms, optionally substituted with O, P, SO$_2$, SO$_3$, and/or Si-containing functionalities,
each $R^2$ is individually selected from halogen (Cl, Br) atoms,
and linear or branched alkyl, aryl, or aralkyl groups with 1-10 carbon atoms, optionally substituted with O, P, SO$_2$, SO$_3$, and/or Si-containing functionalities,
n and m are individually selected from integers in the range 0-5, and n+m is at least 1.

In a more preferred embodiment, n=m=1.

In a further preferred embodiment, $R^1$ and $R^2$ are both alkyl groups with 1-6 carbon atoms. Even more preferably, $R^1$ and $R^2$ are both methyl groups.

Most preferably, the organic peroxide is di(4-methylbenzoyl) peroxide or di(2-methylbenzoyl) peroxide.

The powder mixture comprises at least 20 wt % and most preferably at least 30 wt % of the powdered organic peroxide. The powder mixture comprises at most 80 wt %, more preferably at most 70 wt %, even more preferably at most 60 wt %, and most preferably at most 40 wt % of the powdered organic peroxide.

The powder mixture according to the present invention can be prepared by homogenizing a mixture of the two powders.

Homogeneity can be tested by taking samples from different locations in a batch and analyzing their composition. If the composition of all samples differs by 5% or less, the mixture is considered homogeneous.

Preferably, the mixture is not only homogenized, but also de-agglomerated.

The resulting mixture preferably has an average primary particle diameter (d50) below 500 microns, preferably below 200 microns, most preferably below 100 microns. The term "average primary particle diameter" refers to the volume median (d50). It can be determined with laser light diffraction (a HELOS laser light diffraction analyzer manufactured by SYMPATEC GmbH and equipped with QUIXEL wet dispersion module) using an ultrasonically pre-treated aqueous suspension comprising a surfactant (Teepol CH30) and the particles to be measured in an optical concentration between 5 and 25 wt %.

Various devices can be used to homogenize and/or de-agglomerate the mixture, such as a hammer mill, turbo mill, or pin mill.

In one embodiment, the mixture is homogenized and de-agglomerated at the same time, in the same equipment. In this embodiment, water can be added to the mixture in the form of a water-containing powdered organic peroxide, which is especially preferred for powder mixtures comprising (substituted) dibenzoyl peroxide. For such mixtures, powdered (substituted) dibenzoyl peroxide containing 5-70 wt %, more preferably 10-50 wt %, and most preferably 20-40 wt % of water is milled in the presence of the powdered filler material.

Dibenzoyl peroxide and substituted dibenzoyl peroxides can be safely milled in aqueous slurry and the de-agglomeration step and the homogenization step can therefore be conducted sequentially by (i) de-agglomerating the organic peroxide by milling an aqueous slurry of the organic peroxide in, e.g., a hammer mill, turbo mill, or pin mill, (ii) removing water from the resulting de-agglomerated peroxide, for instance by centrifugation, and (iii) homogenizing the de-agglomerated organic peroxide and the powdered filler material, for instance in a low shear mixer such as a conical screw mixer.

If water is (still) present in the resulting mixture, some of it may be removed during or after milling by evaporation (e.g. by mild heating), until the desired water content is obtained.

The powder mixture, directly after preparation, preferably comprises 0-20 wt %, more preferably 1-15 wt %, and most preferably 5-15 wt % of water. The water content may decline during storage or further processing, which has no or only limited impact on the safety characteristics of the mixture.

The powder mixture according to the present invention finds application as curing agent in coating compositions, in unsaturated polyester resin systems, and in other radically curable thermosetting resin systems (vinyl ester resins, (meth)acrylate resins), and as initiator in a radical polymerization processes, such as the polymerization of (meth)acrylic resins.

EXAMPLES

Example 1

Four powder mixtures of di(4-methylbenzoyl)peroxide and either aluminium trihydroxide (ATH) or magnesium dihydroxide (MDH) were prepared by manually mixing aluminium trihydroxide or magnesium dihydroxide with di(4-methylbenzoyl)peroxide. The resulting mixtures were treated with a hammer mill equipped with a 1.5 mm sieve to obtain a homogeneous mixture.

Composition 1: 60 wt % ATH and 40 wt % di(4-methylbenzoyl)peroxide containing 25 wt % of water.

Composition 2: 67 wt % ATH and 33 wt % dry di(4-methylbenzoyl)peroxide. Di(4-methylbenzoyl)peroxide was dried by air-drying.

Composition 3: 60 wt % MDH and 40 wt % di(4-methylbenzoyl)peroxide containing 25 wt % of water.

Composition 4: 67 wt % MDH and 33 wt % dry di(4-methylbenzoyl)peroxide. Di(4-methylbenzoyl)peroxide was dried by air-drying.

Comparative Example

Four different compositions of di(4-methylbenzoyl)peroxide and barium sulphate were prepared by manually mixing barium sulphate with di(4-methylbenzoyl)peroxide. The resulting mixtures were treated with a hammer mill equipped with a 1.5 mm sieve to obtain a homogeneous mixture.

The compositions differed in water content and type of barium sulphate (natural or synthetic).

Composition A: 60 wt % synthetic $BaSO_4$ (Blanc Fixe micro, ex. Sachtleben Chemie GmbH; d50=0.7 microns) and 40 wt % di(4-methylbenzoyl)peroxide. containing 25 wt % of water.

Composition B: 67 wt % synthetic $BaSO_4$ (Blanc Fixe micro, ex. Sachtleben Chemie GmbH; d50=0.7 microns) and 33 wt % dry di(4-methylbenzoyl)peroxide.

Composition C: 60 wt % natural $BaSO_4$ (CIMBAR UF, ex CIMBAR Performance Minerals; d50=1.6-5.8 microns) and 40 wt % di(4-methylbenzoyl)peroxide containing 25 wt % of water Composition D: 67 wt % natural $BaSO_4$ (CIMBAR EX, ex CIMBAR Performance Minerals; d50=0.8-1.4 microns) and 33 wt % dry di(4-methylbenzoyl)peroxide.

Example 2

The compositions of Example 1 and the Comparative Example were submitted to several tests in order to assess their explosiveness, impact sensitivity, explosive power, and burning behaviour. The results are displayed in Table 1.

Thermal Explosiveness

The Dutch Pressure Vessel Test (PVT), UN test E2, was used to check the thermal explosiveness of the compositions. Samples were heated under defined confinement in a steel vessel, equipped with a bursting disc. The vent opening of the vessel could be varied. The minimum opening, at which the decomposition in the vessel just cannot be vented without rupture of the bursting disc, is called the limiting diameter. The experiments were carried out with either 10 or 50 gram composition.

BAM Impact-Hammer Test

The test was performed according to UN test 3(a)(ii) and EC test A14, part impact sensitivity, six trials per energy level starting at 40 J. Where necessary, tests at 7.5 J and 20 J were performed. The results were considered positive if an explosion, report, or flame occurred at least once at a particular energy level. The result was considered negative if no reaction or only decomposition (change of colour or smell) occurred in six trials at a particular energy level.

Modified Trauzl Test

The test was performed according to UN test F.4. This test was used to measure the explosive power of the compositions. A detonator was initiated in the substance whilst the substance was confined in a hole in a lead block. A 6.0 g sample was placed in the sample vial, which was assembled as required and placed in the lead block. The lead block was placed on a solid surface in a protected area, the blasting cap was fully inserted and, when the area was vacated, the cap was fired. The volume of the cavity in the lead block was measured accurately, to the nearest 0.2 ml, using water before and after the test. Three tests were conducted on the compositions and on an inert reference substance using the same type of assembly.

Burning and Deflagration Tests

In these tests, a strip of 20×2 cm of the composition was applied on a flat stainless steel plate.

In the burning tests, the strips were ignited by a yellow or blue gas flame.

In the deflagration tests, the strips were ignited by a hot steel rod. The steel rod, which was heated with a Bunsen burner until red glowing, was pushed into the substance.

In both tests, it was observed whether decomposition (hissing, puffing), ignition or melting occurred and whether the substance continued burning or not. The time required to affect the entire 20 cm strip was measured.

|  | Synthetic BaSO4 | | Natural BaSO4 | | ATH | | MDH | |
| --- | --- | --- | --- | --- | --- | --- | --- | --- |
|  | A (wet) | B (dry) | C (wet) | D (dry) | 1 (wet) | 2 (dry) | 3 (wet) | 4 (dry) |
| PVT (mm) | <1 (50 g) | <1 (10 g) | <1 (10 g) | 1 (10 g) | <1 (50 g) | <1 (10 g) | <1 (50 g) | <1 (50 g) |
| Impact (J) | >40 | >40 | >40 | >7.5 <20 | >40 | >40 | >40 | >40 |
| Burning time (sec) | nd | 3-4 | stops | 2 | no ignition | 42 | stops | 238 |
| Deflagration time (sec) | nd | 30 | stops | 7 | stops | 260 | stops | >296 sec stopped at 16 cm |
| Modified Trauzl (ml) | 4.0 | 4.8 | 3.6 | 4.4 | 1.8 | 1.8 | 1.8 ml | 2.4 ml | nd = not determined

The results show that peroxide formulations based on ATH and MDH are safer than the same formulations on synthetic or natural $BaSO_4$.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A powder mixture comprising:
   20-80 wt % of one or more di(methylbenzoyl)peroxides,
   20-80 wt % of a powdered filler material consisting of a solid inorganic flame retardant chosen from aluminum trihydroxide, magnesium dihydroxide, and combinations thereof, and
   0-20 wt % water,
   wherein the total of the one or more di(methylbenzoyl) peroxides and the powdered filler material equals 100 parts by weight.

2. The powder mixture according to claim 1 wherein the one or more di(methylbenzoyl) peroxides is di(4-methylbenzoyl) peroxide.

3. The powder mixture according to claim 1, wherein the one or more di(methylbenzoyl) peroxides is di(2-methylbenzoyl) peroxide.

4. A process for preparing the powder mixture according to claim 1, comprising the step of homogenizing the one or more di(methylbenzoyl) peroxides and the powdered filler material.

5. The process according to claim 4, wherein the homogenized powder mixture has an average particle diameter (d50) below 500 microns.

6. The process according to claim 4, wherein the powdered organic peroxide contains 0 to 25 wt % of water.

7. The process according to claim 4, comprising the steps of:
   milling the one or more di(methylbenzoyl) peroxides in an aqueous slurry to de-agglomerate the one or more di(methylbenzoyl) peroxides,
   removing water from the resulting de-agglomerated one or more di(methylbenzoyl) peroxides, and
   homogenizing the de-agglomerated one or more di(methylbenzoyl) peroxides and the powdered filler material.

8. A process for curing a radically curable thermosetting resin, comprising using the powder mixture according to claim 1 as a radical initiator in the process.

9. The process according to claim 8, wherein the radically curable thermosetting resin is a coating composition.

10. A radical polymerization process comprising initiating polymerization with a powder mixture comprising:
    20-80 wt % of one or more di(methylbenzoyl)peroxides,
    20-80 wt % of a powdered filler material consisting of a solid inorganic flame retardant chosen from aluminum trihydroxide, magnesium dihydroxide, and combinations thereof, and
    0-20 wt % water,
    wherein the total of the one or more di(methylbenzoyl) peroxides and the powdered filler material equals 100 parts by weight.

11. The process according to claim 4, wherein the resulting powder mixture has an average particle diameter (d50) below 200 microns.

12. A powder mixture comprising:
    33 to 40 wt % of a peroxide chosen from di(4-methylbenzoyl)peroxide, di(2-methylbenzoyl)peroxide, or combinations thereof,
    60 to 67 wt % of aluminum trihydroxide, magnesium dihydroxide, or combinations thereof, and
    0 to 10 wt % water based on a total weight of the peroxide,
    wherein the total of the peroxide and the aluminum trihydroxide, magnesium dihydroxide, or combinations thereof equals 100 parts.

13. The powder mixture according to claim 12 consisting of:
    40 wt % of di(4-methylbenzoyl)peroxide,
    60 wt % aluminum trihydroxide, and
    10 wt % water based on a total weight of the peroxide,
    wherein the total of the peroxide and the aluminum trihydroxide equals 100 parts.

14. The powder mixture according to claim 12 consisting of:
    33 wt % of di(4-methylbenzoyl)peroxide, and
    67 wt % aluminum trihydroxide.

15. The powder mixture according to claim 12 consisting of:
    40 wt % of di(4-methylbenzoyl)peroxide,
    60 wt % magnesium dihydroxide, and
    10 wt % water based on a total weight of the peroxide,
    wherein the total of the peroxide and the magnesium dihydroxide equals 100 parts.

16. The powder mixture according to claim 12 consisting of:
    40 wt % of di(4-methylbenzoyl)peroxide, and
    60 wt % magnesium dihydroxide.

* * * * *